United States Patent [19]

Gupta et al.

[11] 4,404,302
[45] Sep. 13, 1983

[54] ACYLATED HINDERED HEXAHYDROPYRIMIDINES AND THEIR USE AS LIGHT STABILIZING AGENTS

[75] Inventors: Goutam Gupta, Homewood, Ill.; Chester E. Ramey, Chagrin Falls, Ohio

[73] Assignee: Ferro Corporation, Cleveland, Ohio

[21] Appl. No.: 382,556

[22] Filed: May 27, 1982

[51] Int. Cl.³ .......... C08K 5/34; C07D 237/00; C07D 237/02; C07D 239/02
[52] U.S. Cl. .......... 524/100; 524/102; 524/86; 544/242; 544/245; 544/335
[58] Field of Search .......... 544/242, 245, 335; 524/100, 102

[56] References Cited

U.S. PATENT DOCUMENTS

| | | | |
|---|---|---|---|
| 2,525,855 | 10/1950 | Bergmann | 544/231 |
| 3,872,120 | 3/1975 | Mod et al. | 544/335 |
| 3,875,159 | 4/1975 | Mod et al. | 424/251 |
| 3,899,491 | 8/1975 | Ramey et al. | 544/231 |
| 3,910,948 | 10/1975 | Mod et al. | 548/300 |
| 3,928,330 | 12/1975 | Ramey et al. | 544/225 |
| 4,007,156 | 2/1977 | Ramey et al. | 524/100 |
| 4,058,528 | 11/1977 | Gaudette et al. | 544/335 |
| 4,104,249 | 8/1978 | Alink et al. | 524/89 |
| 4,146,714 | 3/1979 | Alink | 544/242 |

FOREIGN PATENT DOCUMENTS

| | | | |
|---|---|---|---|
| 500635 | 3/1959 | Canada | 544/335 |
| 1363904 | 5/1964 | France | 544/335 |

OTHER PUBLICATIONS

Helvetica Chimica Acta 30, 1114 (1947).

*Primary Examiner*—John Kight, III
*Assistant Examiner*—Kriellion Morgan

[57] ABSTRACT

An acylated, hindered hexahydropyrimidine of the formula

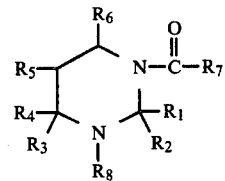

wherein
$R_1$, $R_2$, $R_3$ and $R_4$ may be the same or different independently of each other and are alkyl having 1 to 6 carbon atoms, when unsubstituted, or alkyl or aryl substituted;
$R_5$ and $R_6$ may be the same or different and are hydrogen, or alkyl;
$R_7$ is selected from the group consisting of: alkyl having 1 to 20 carbon atoms, substituted alkyl where the alkyl without substitution has 1 to 20 carbon atoms and where substituents may be up to five lower alkyl groups, arylalkyl, cycloalkyl having 3 to 12 carbon atoms, aryl aryl substituted with 1 to 3 substituents seleted from the group consisting of: lower alkyl, lower alkoxy, and hydroxyl;

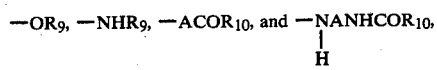

wherein
$R_9$ is unsubstituted or substituted with alkyl,
$R_{10}$ is hydroxyl, lower alkoxy, phenoxy and the group

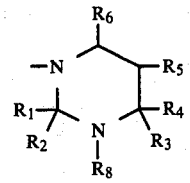

and
$R_8$ is hydrogen, alkyl, substituted alkyl, arylalkyl, hydroxyl, oxyl and

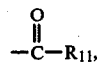

wherein $R_{11}$ is unsubstituted or substituted alkyl.

35 Claims, No Drawings

ACYLATED HINDERED HEXAHYDROPYRIMIDINES AND THEIR USE AS LIGHT STABILIZING AGENTS

BACKGROUND OF THE INVENTION

Synthetic as well as natural polymeric materials are degraded in appearance and properties by exposure to high-energy solar radiation, especially that occurring in the ultraviolet or near ultraviolet region of the spectrum. The energy content of the light in this region is sufficient to cause breakage of bonds in organic molecules, including polymeric molecules.

Absorption of light by a polymeric molecule ultimately may cause the polymer to become crazed, to chalk, to become discolored, to lose gloss, to have a reduction of physical properties, or a combination of two or more of these effects. Continued exposure eventually may lead to embrittlement. However, polymers react to light in different ways. Polymers such as polyvinyl fluoride are quite resistant to light deterioration, whereas polyolefins deteriorate rapidly.

Through the years many different types of stabilizers for polymers have been utilized with varying degrees of success. Benzophenones, benzotriazoles, and aryl esters of organic acids are some of the earlier ultraviolet stabilizers used. These compounds differed as to the type of polymeric compound they protected and against which wavelengths they were effective.

The prior art compounds, such as the benzophenones and benzotriazoles, act as light stabilizers through the preferential absorption of light in the ultraviolet or near ultraviolet region of the spectrum. The energy of the light is dissipated as heat by the stabilizer, without damage to the polymer. However, these U.V. absorbers are useful only in articles with a substantial cross section, to allow for the light absorption at reasonable use concentrations, and are not useful for fine fibers or thin films of the polymer. The aryl esters of organic acids are also U.V. absorbers, and are slowly destroyed on exposure to light, thus their effectiveness diminishes over a period of time.

Piperidine and piperazine derivatives have also been utilized as ultraviolet stabilizers with some degree of success, as in U.S. Pat. Nos. 3,899,491, 3,928,330, and 4,007,156, but still retain some of the disadvantages of their predecessors.

Hexahydropyrimidines have been utilized, in the past, as antioxidants in natural and synthetic rubbers, see U.S. Pat. No. 4,104,249. Hexahydropyrimidines have also been utilized as accelerators for rubber vulcanization, a cross-linking reaction, which would appear to suggest a property which is opposite to the light stabilization property of this invention.

In many cases natural and synthetic rubbers, such as those with which U.S. Pat. No. 4,104,249 is concerned, include carbon black as one of the formulation components. The carbon black present has many functions including being an ultraviolet light absorber. There was no necessity therefore for the anti-oxidant to be also an ultraviolet absorber or for the composition to include a separate, added light absorber. Compounds normally do not possess both anti-oxidant and ultraviolet light absorption properties.

The hexahydropyrimidines of U.S. Pat. No. 4,104,249 are very susceptible to hydrolysis in the air during storage and compounding and also to degradation during processing. The compounds were not considered useful as light stabilizers. In addition to their instability due to hydrolysis, the compounds were of low molecular weight, leading to undesirable volatility during processing.

Hexahydropyrimidines have also been utilized as bactericides and fungicides, U.S. Pat. Nos. 3,872,120 and 3,875,159; as corrosion inhibitors, U.S. Pat. No. 4,146,714; and for their pharmacological activity.

U.S. Pat. No. 3,910,948 describes N,N'-diacyl derivatives of hexahydropyrimidine, and discloses that they are useful as mold growth inhibitors. The compounds disclosed exhibited both selective and broad antimycotic activity, depending upon chemical structure. Some of the compounds exemplified were 1,3-diacetylhexahydropyrimidine, 1,3-dibutyrylhexahydropyrimidine, 1,3-dipalmitoylhexahydropyrimidine, and the like.

Japanese Patent Publication (Kokai) No. 1974-53575, published May 24, 1972, describes anti-deterioration agents that are suggested for use in polyethylene, polypropylene, many vinyl polymers, polyesters, polystyrenes, and polyamides. These agents are apparently intended to improve the light stability of the polymers. The agents are 4,6,6-trimethylhexahydropyrimidine derivatives of the general formula

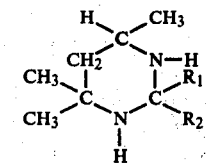

where $R_1$ and $R_2$ are the same or different alkyl groups, allyl groups, or aralkyl groups, which groups have from 1 to 18 carbons, and where $R_1$ and $R_2$, along with the ring carbon to which they are attached, may together form a 4- to 7-membered alicyclic ring, or with a hetero atom may constitute a hetero-alicyclic structure. Structures such as these are very susceptible to hydrolysis, regenerating $R_1R_2C=O$ and the corresponding diamine. Hence they are subject to rapid degradation during handling. In addition, when $R_1$ and $R_2$ are lower alkyl groups, the structure is likely to be lost easily from the host polymer matrix through volatilization, because of the low molecular weight of the structure.

Some of the chemistry and chemical reactions of hexahydropyrimidines are described in Helvetica Chimica Acta 30, 1114 (1947), and J. Prakt. Chemie 38, 339 (1965).

SUMMARY OF THE INVENTION

It has now been found that certain acylated hindered hexahydropyrimidines exhibit exceptional light stabilizing properties, without the disadvantages of the prior art compounds, and can be utilized to protect a wider range of polymeric compounds than has hereto been possible.

Thus, acylated hindered hexahydropyrimidines of the general formula

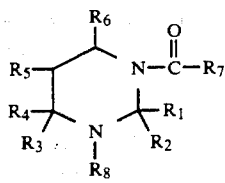

show light stabilization properties and can be utilized as such in the protection of many polymeric materials including polyvinyl halides, poly α-olefins, polydienes, polyamides and polystyrene.

In the formula above:

$R_1$, $R_2$, $R_3$ and $R_4$ may be the same or different and are selected from the group consisting of: alkyl having 1 to 6 carbon atoms unsubstituted, or substituted with one methyl, ethyl or phenyl group, aryl, and aryl substituted with 1 to 3 substituents selected from the group consisting of lower alkyl, lower alkoxy, and hydroxyl, and wherein $R_1$ together with $R_2$, and $R_3$ together with $R_4$, each taken together with the respective ring carbon to which they are attached, may form respectively a cycloalkyl group of ring size from 4 to 7 carbons;

$R_5$ and $R_6$ may be the same or different and are selected from the group consisting of hydrogen, and alkyl having 1 to 6 carbon atoms, and $R_5$ together with $R_6$ and the two ring carbons to which they are attached respectively may form a cycloalkyl group of ring size from 5 to 7 carbon atoms;

$R_7$ is selected from the group consisting of: alkyl having 1 to 20 carbon atoms, substituted alkyl where the alkyl without substitution has 1 to 20 carbon atoms and where the substituents may be up to five lower alkyl groups, cycloalkyl having 3 to 12 carbon atoms, aryl, aryl substituted with 1 to 3 substituents selected from the group consisting of lower alkyl, lower alkoxy, and hydroxyl, $$-OR_9, \quad -NHR_9, \quad -ACOR_{10}, \text{ and } -\underset{H}{N}ANHCOR_{10},$$

wherein $R_9$ is selected from the group consisting of alkyl having 1 to 20 carbon atoms unsubstituted, or substituted with up to 5 lower alkyl groups, cycloalkyl having 5 to 11 carbons, and phenyl; wherein A is: alkylene of 1 to 12 carbons; alkylene substituted with alkyl or alkenyl to have a total of up to 18 carbons; alkenylene of 2 to 4 carbons; cycloalkylene up to 12 carbon atoms; cycloalkenylene up to 12 carbon atoms; bicycloalkylene up to 8 carbon atoms; bicycloalkenylene up to 8 carbon atoms; or phenylene, and wherein $R_{10}$ is selected from the group consisting of hydroxyl, lower alkoxy, phenoxy, and the group

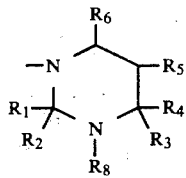

wherein $R_1$, $R_2$, $R_3$, $R_4$, $R_5$, and $R_6$ are as defined above, and $R_8$, wherever it occurs above, is selected from the group consisting of hydrogen, alkyl having 1 to 10 carbon atoms, arylalkyl, hydroxyl, oxyl and

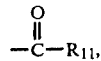

wherein $R_{11}$ is selected from the group consisting of alkyl having 1 to 20 carbon atoms unsubstituted, or substituted with up to five lower alkyl groups, and aryl.

When $R_{10}$ is hydroxyl, metal salts can be formed from this carboxylic acid which are useful as light stabilizers, such as the salts of nickel, cobalt, and barium.

DETAILED DESCRIPTION OF THE INVENTION

This invention is directed to acylated hindered hexahydropyrimidines having the formula above, which are useful as light stabilizers.

The acylated, hindered hexahydropyrimidines of the invention are useful for the stabilization of polymeric materials that normally tend to deteriorate upon exposure to light. They are ordinarily used in the amount of from about 0.01% to 5% by weight in stabilized polymeric compositions, based on the polymer content of the stabilized composition, by weight.

This invention also relates to compositions of matter which are stabilized against ultraviolet light deterioration and which comprise a synthetic organic host polymer that is normally subject to ultraviolet deterioration containing as an additive a stabilizer according to the invention, in an amount from about 0.01% to 5% by weight based on the weight of the host polymer, and preferably from 0.1% to 2% by weight.

The stabilizers of this invention are suitable for the protection of many synthetic polymers from the deleterious effects of light. Homopolymers, copolymers and mixtures thereof are embraced within the scope of the substrates which may be stabilized with the stabilizers of this invention, among which may be mentioned polystyrene and including homopolystyrene and copolymers with acrylonitrile and/or butadiene; vinyl resins formed from the polymerization of vinyl halides or from copolymerization of vinyl halides and unsaturated polymerizable compounds, for example, vinyl esters, α,β-unsaturated acids, α,β-unsaturated esters, and unsaturated hydrocarbons such as butadienes and styrene; poly-α-olefins such as high and low density polyethylene, cross-linked polyethylene, polypropylene, poly(4-methylpentene-1), polybutene-1, and the like including copolymers of poly-α-olefins such as ethylene-propylene copolymers, copolymers of ethylene and vinyl acetate, and the like; polydienes such as polybutadiene and polyisoprene; polyurethanes such as are prepared from polyols and organic polyisocyanates, polyamides such as poly(hexamethylene-adipamide); polycarbonates such as those prepared from bisphenol-A and phosgene; polyacetals; and polyacrylics such as polyacrylonitrile, and the like. Particularly preferred polymers for the compositions of this invention are those normally solid polymers of alpha-olefins having up to 4 carbon atoms, e.g., ethylene, propylene, butene, and their copolymers.

The stabilized polymers of the present invention have utility in the normal uses for which plastics are employed and are particularly useful for film and fiber. Compounds of this invention may be incorporated in the polymeric substance during the usual processing operations, for example, by hot milling, the composition then being extruded, pressed, blow molded or the like into films, fibers, filaments, hollow spheres and the like. Where the polymer is prepared from a liquid monomer as in the case of styrene, the stabilizer may be dispersed or dissolved in the monomer prior to polymerization or curing.

The compounds of the invention can be used in combination with other stabilizers such as: thio esters, of which distearyl thio dipropionate and dilauryl thio dipropionate are exemplary; phosphites, such as di- and tri-alkyl and -arylalkyl phosphites, as well as other phosphites such as distearyl pentaerythritol diphosphite; heat stabilizers; other ultraviolet light stabilizers, antiozonants, and antioxidants.

Compounds of this invention can be used alone or they may be used in combination with other ultraviolet light stabilizers such as, for example 2(2-hydroxyphenyl)benzotriazoles, 2-hydroxybenzophenones, salicylates, nickel complexes, and particularly, the benzoates, such as 2,4-di-t-butyl-phenyl-3,5-di-t-butyl-4-hydroxy benzoate.

Also, in addition to the actinic stabilizers described, the plastic compositions may also contain other additives such as plasticizers, pigments, fillers such as talc or other minerals, dyes, glass or other fibers, metal chelating agents, dyesites, corrosion and rust inhibitors, dispersing agents, carbon black or other pigments, lubricants, anti-block or anti-slip agents, thermal antioxidants, and the like. For example, in most applications, it is desirable to incorporate into the resin composition sufficient thermal antioxidants to protect the plastic against thermal and oxidative degradation. The amount of antioxidant required will be roughly comparable to that of the actinic stabilizer, namely, from about 0.005% to 5% and preferably from 0.01% to 2% by weight of the polymer. Representative of such antioxidants are phosphite esters, such as triphenylphosphite and dibutylphosphite and alkyl arylphosphites such as dibutylphenylphosphite, and the like, as pointed out above.

Good results are also obtained when the thermal antioxidant employed, in conjunction with a light stabilizer according to the invention, is one of the hindered phenols. These compounds have been found to provide good thermal stabilization with very low discoloration in compositions stabilized according to the invention. Typical of these hindered phenolic antioxidants are the following most preferred co-stabilizers:

1. 2,6-di-tert-butyl-4-methyl phenol
2. 2,6-di-tert-butyl phenol
3. 2,2'-methylene-bis(6-tert-butyl-4-methyl phenol)
4. n-octadecyl-3-(3,5-di-tert-butyl-4-hydroxyphenyl) propionate
5. 1,1,3-tris(3-tert-butyl-6-methyl-4-hydroxyphenyl) butane
6. pentaerythrityl tetra kis[3-(3,5-di-tert butyl-4-hydroxyphenyl) propionate]
7. di-n-octadecyl-(3,5-di-tert-butyl-4-hydroxybenzyl) phosphonate
8. 2,4,6-tris(3,5-di-tert-butyl-4-hydroxybenzyl) mesitylene
9. tris(3,5-di-tert-butyl-4-hydroxybenzyl)isocyanurate.

The above phenolic antioxidants are known and many are commercially available and are used in the amount from about 0.025% to 5%, and preferably 0.01% to 2% by weight, based on the polymer. A more complete description of these hindered phenols appears in U.S. Pat. No. 4,007,157, from col. 3, line 10, through col. 8, line 25, which description is incorporated herein by reference.

In a preferred series of compounds of this invention, in the general formula above, $R_1$, $R_2$, $R_3$ and $R_4$ may be the same or different and are selected from the group consisting of alkyl having 1 to 6 carbon atoms; and $R_1$ together with $R_2$, and $R_3$ together with $R_4$, each taken together with the respective ring carbon to which they are attached, may form respectively a cycloalkyl group of 5 to 6 carbons;

$R_5$ and $R_6$ may be the same or different and are selected from the group consisting of hydrogen, and alkyl having 1 to 6 carbon atoms, and $R_5$ together with $R_6$ and the two ring carbons to which they are attached respectively may form a cycloalkyl group having 5 or 6 carbons;

$R_7$ is selected from the group consisting of alkyl having 1 to 20 carbon atoms, substituted alkyl where the alkyl without substitution has 1 to 20 carbon atoms and where the substituents may be up to five lower alkyl groups, arylalkyl, aryl, substituted aryl, —$OR_9$, —$NHR_9$, the group —$(CH_2)_nCOR_{10}$ where n is 1 to 12, and

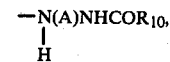

wherein $R_9$ is selected from the group consisting of alkyl having 1 to 20 carbon atoms unsubstituted, or substituted with up to five lower alkyl groups, and phenyl, and $R_8$ is selected from the group consisting of hydrogen, lower alkyl, hydroxyl, oxyl, and

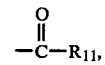

wherein $R_{11}$ is selected from the group consisting of alkyl having 1 to 20 carbon atoms unsubstituted, or substituted with up to five lower alkyl groups, and aryl, and where the meanings of $R_9$, $R_{10}$, and A, are the same as in the general formula above.

The most preferred group of compounds of this invention are those wheren $R_1$, $R_2$, $R_3$, $R_4$ and $R_6$ are each methyl, $R_5$ is hydrogen, $R_7$ is selected from the group consisting of alkyl having 1 to 20 carbon atoms, substituted alkyl where the alkyl without substitution has up to 20 carbon atoms and where the substituents may be up to five lower alkyl groups, aryl, aryl substituted with 1 to 3 substituents selected from the group consisting of lower alkyl, lower alkoxy, and hydroxyl, —$OR_9$, —$NHR_9$ and the group —$(CH_2)_nCOR_{12}$, wherein $R_{12}$ is the radical

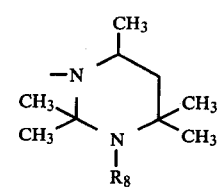

and $R_8$ is selected from the group consisting of hydrogen, alkyl having 1 to 4 carbon atoms, hydroxyl and oxyl.

The general preparation of hexahydropyrimidines is known in the art (see U.S. Pat. No. 2,525,855) and includes the reaction of 1,3-diaminopropane derivatives with an aldehyde or ketone according to the following general equation:

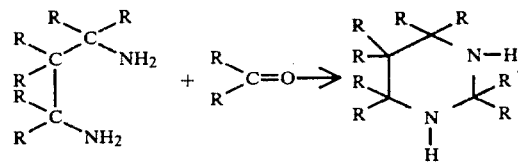

wherein R is the same or different and may be hydrogen or a substituent.

The hexahydropyrimidines may also be prepared by the reaction of an α,β-unsaturated ketone together with ammonia and a second ketone, to form a tetrahydropyrimidine according to the following general equation:

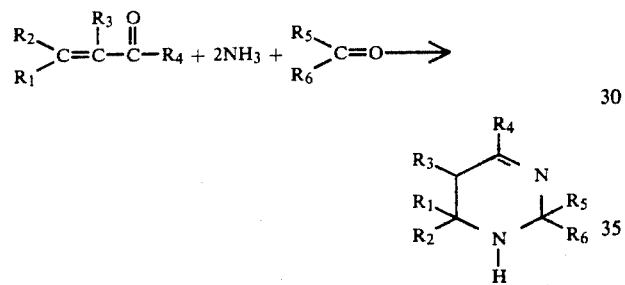

followed by reduction of the tetrahydropyrimidine with sodium metal and alcohol or catalytic hydrogenation.

The most preferred compounds of this invention are derivatives of hexahydro-2,2,4,4,6-pentamethylpyrimidine of the formula

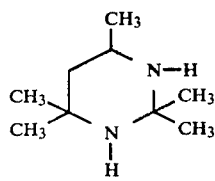

These may be prepared by several different reactions such as

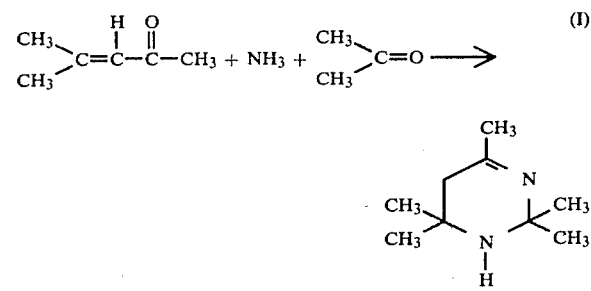

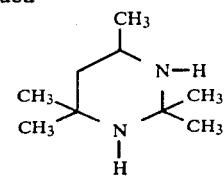

The reaction of ammonia with acetone to form the tetrahydro derivative of the pentamethylpyrimidines and its reduction to the hexahydro derivative utilizing sodium and alcohol is discussed in the earlier literature including Bradbury et al., J.Chem.Soc. [1947]1394.

The general reaction of diamines, such as the reaction of 1,3-propanediamine with aldehydes or ketones, is discussed in "The Pyrimidines", Interscience Publishers [1962], pp. 452-454, and in Japan Kokai No. 53575 (May 24, 1972).

Acylation of the hexahydropyrimidine derivatives in accordance with the invention is necessary to provide hydrolytic and thermo-oxidative stability. The unacylated hexahydropyrimidines are extremely reactive toward water, carbon dioxide, and air, according to Bradbury et al. Acylation of the hexahydropyrimidines is accomplished according to the following general reactions, to yield the products indicated:

(1) reaction with an acid chloride, RCOCl, yielding an amide;

(2) reaction with a chloroformate, Cl—COOR, yielding a urethane;

(3) reaction with an isocyanate, RNCO, yielding a urea;

(4) reaction with a ketene, $RRC{=}C{=}O$, yielding an amide;

(5) reaction with an ester, with loss of alcohol, to yield an amide;

(6) reaction with a carboxylic acid, with loss of water, to yield an amide; and (7) reaction with an anhydride to yield an amide.

The following examples are illustrative procedures for the preparation of the compounds of this invention. Parts and percentages are by weight, and temperatures are expressed in degrees Celsius, unless otherwise stated. The first eight examples describe the preparation of chemical intermediates; the remaining examples describe the production of useful light stabilizing compounds.

EXAMPLE 1

Preparation of a Tetrahydropyrimidine (THP) from Acetone and Ammonia Catalyzed by Calcium Chloride and Ammonium Chloride A resin kettle contained a stirred mixture of 96.7 g. (1.66 mole) acetone, 3.3 g. ammonium chloride, and 13.3 g. anhydrous calcium chloride (cooled with dry ice). 36.6 g. of liquid ammonia was distilled into the stirred mixture over a 2 hour period. The reactor was sealed, and stirred for 3 days, upon which two layers formed. The upper layer, a yellow liquid with an ammoniacal odor, solidified upon freezer storage, giving 82.1 g. (86% yield) of 2,2,4,4,6-pentamethyl-2,3,4,5-tetrahydropyrimidine monohydrate, with m.p. 30°-40° C.

EXAMPLE 2

Preparation of a THP from Acetone and Mesityl Oxide

In a pressure reactor was placed a mixture of 196 grams mesityl oxide and 137 grams acetone. To this mixture was added, over a 5 hour period, 88 grams of ammonia gas at a rate such that the autogeneous pressure did not exceed 70 psi. The mixture was stirred for an additional 18 hours after completion of ammonia addition. The resulting mixture was distilled, under reduced pressure, to yield a product, $b_{20}$ 63°–66° C.

Anal. Calc'd. for $C_9H_{18}N_2$:N, 18.18; Found: N, 17.97.

EXAMPLE 3

Preparation of THP from Acetone, Mesityl Oxide, and Ammonia 627.2 g. (6.390 mole) of mesityl oxide and 438.4 g. (7.55 mole) of acetone were charged to a steel autoclave. The bomb was cooled to 0° C., and anhydrous ammonia (568.6 g., 34.45 mole) was charged to the reaction, while the temperature was maintained below 20° C.

The mixture was stirred for 66 hours, after which the bomb was opened and the mixture poured out to give 1861.7 g. of a yellow cloudy liquid containing much dissolved $NH_3$. A sample, degassed via nitrogen purge and dried with a 4 A molecular sieve, was analyzed at 89.7% 2,2,4,4,6-pentamethyl-2,3,4,5-tetrahydropyrimidine by gas chromatography.

EXAMPLE 4

Preparation of 2,4-Diamino-2-Methylpentane

A solution of diacetoneamine in water containing excess ammonia was prepared according to the procedure of Lai et al., J. Org. Chem. 46, 323–327 (1981). This solution was analyzed by amine equivalent before and after evacuation to determine the relative amounts of diacetoneamine and ammonia.

To 212.4 g. of the original solution was added 90.6 g. of concentrated aqueous ammonia, to provide a twofold molar excess of ammonia to diacetoneamine.

A suspension of aluminum amalgam was prepared by treating 30 g. of aluminum metal (20 mesh and finer) in 130 ml. distilled water with 1 g. of mercuric chloride, with stirring. The amalgam suspension was cooled to 0°, when the premixed solution of ammonia and diacetoneamine was gradually added by means of a dropping funnel. Intermittent cooling with a dry ice/isopropanol bath was used to maintain the temperature at 15°–70°. After four hours, the suspension was stirred at room temperature overnight.

The next day the reduction was completed by heating at 90° for one hour. After separating the formed alumina from the aqueous solution of product by filtration, the solution was basified with 30 g. of sodium hydroxide pellets. The organic layer was separated and the aqueous phase extracted twice with 100 ml. portions of methylene chloride. The extracts were combined with the organic layer and dried over anhydrous sodium sulfate. After evaporation of the methylene chloride, the residue was distilled over a fractionating column to provide a fraction b.p. 65°–68° at a pressure of 24–25 mm Hg. It was shown to be free of carbonyl absorption by infrared spectroscopy and to contain 2,4-diamino-2-methylpentane by gas chromatography.

EXAMPLE 5

Hydrogenation of THP

A sample of 27.4 grams 2,2,4,4,6-pentamethyl-2,3,4,5-tetrahydropyrimidine was dissolved in 50 grams of ethanol. To the ethanolic solution was added 6.9 grams of sodium metal at such a rate that a temperature of 70°–80° C. was maintained. After the addition was completed, the mixture was heated for one hour at 85°–95° C. The mixture was allowed to cool to room temperature and water added to the mixture. The organic layer was extracted with toluene, the toluene extract washed with water, dried, and the toluene removed, yielding 2,2,4,4,6-pentamethyl-hexahydroprimidine.

EXAMPLE 6

Raney Nickel Reduction of THP to Hexahydropyrimidine (HHP)

A solution of 15.43 g. (0.1000 mole) 2,2,4,4,6-pentamethyl-2,3,4,5-tetrahydropyrimidine in 200 ml. anhydrous methanol was charged to a 1 liter stainless steel autoclave. 0.96 g. (1.6 ml. settled catalyst, 6.2% by weight) W-2 Raney nickel catalyst were then charged to the reactor, in 50 ml. anhydrous methanol. The mixture was then hydrogenated at 100° C. and 600 psi for 6 hours. Removal of catalyst and solvent, and distillation of the brown-yellow crude oily product afforded 7.64 g. (48.9%) 2,2,4,4,6-pentamethyl hexahydropyrimidine (b.p. 74° C.–84° C. at 15–16 mm Hg).

EXAMPLE 7

Cyclohexanone Analog of a HHP

To a stirred mixture of 49.08 g. (0.50 mole) cyclohexanone and 9.46 g. (0.1849 mole) 90% formic acid, cooled to 0° C., 9.78 g. liquid ammonia (0.5743 mole) was added dropwise over a 10 minute period and stirred overnight, while allowing the mixture to come to room temperature.

The mixture was stripped of water, formic acid, and excess cyclohexanone at 140° C./20 mm. Hg for 1 hour; the resulting brown oil was then distilled to give 9.80 g. (7.09% yield) of 2,4-dipentamethylene-5,6-tetramethylene hexahydropyrimidine (b.p. 154° C.–158° C. at 0.4 mm. Hg).

EXAMPLE 8

Reaction of Stearoyl Chloride with a HHP to form a Stearamide

Five grams (5 gms., 0.032 mole) 2,2,4,4,6-pentamethylhexahydropyrimidine was dissolved in 50 ml. dry ether. To this solution was added dropwise 9.17 gm. (0.032 mole) stearoyl chloride dissolved in 25 ml. ether. The resulting mixture solidified. Saturated aqueous sodium bicarbonate was added to the mixture and then the mixture was extracted with methylene chloride. The methylene chloride extract was washed, dried (anhydrous magnesium sulfate) and the solvent removed, yielding the product. Mp 69°–70° C.

The resulting stearamide can be depicted by the formula and described by the name:

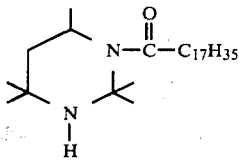

1-(stearoyl)2,2,4,4,6-pentamethyl hexahydropyrimidine (hereafter, Compound 8).

By substituting an equivalent amount of propionyl chloride for the stearoyl chloride used in the above example, there is produced: 1-(propionyl)2,2,4,4,6-pentamethyl HHP.

Similarly, cyclohexane carbonyl chloride may be used, for the production of 1-(cyclohexane carbonyl)2,2,4,4,6-pentamethyl HHP.

Similarly, other alkanoyl chlorides may be used as in this example, to produce members of the family 1-(alkanoyl)2,2,4,4,6-pentamethyl hexahydropyrimidine.

EXAMPLE 9

Acylation of a HHP with Sebacoyl Chloride

To a solution of 8.0 g. (0.0513 mole) 2,2,4,4,6-pentamethyl hexahydropyrimidine in 150 ml. dry toluene was added dropwise 6.13 g. (0.0256 mole) of sebacoyl chloride in 50 ml. toluene, resulting in an exothermic reaction, and the formation of a precipitate. An additional 50 ml. of dry toluene was added, and the mixture was then stirred for 18 hours, and then filtered, collecting the precipitate.

The collected solid material was slurried in saturated aqueous sodium bicarbonate, affording two layers. The aqueous layer was evaporated to dryness, and the resulting solid was then digested with CH$_2$Cl$_2$, filtered, and the solvent removed to yield 9.86 g. (80.4% yield) of a yellowish-white solid, hereafter Compound 9, m.p. 137° C.–139° C., having the formula:

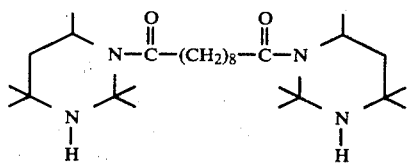

1,1'-sebacoyl bis-(2,2,4,4,6-pentamethyl hexahydropyrimidine.

By substituting an appropriate amount of succinoyl chloride for the sebacoyl chloride used above, there is obtained 1,1'-succinoyl bis(2,2,4,4,6-pentamethyl HHP). Similarly, the chlorides of the following could be used:
dodecane succinic acid
methyl succinic acid
itaconic acid
dodecene succinic acid
fumaric acid
cyclohexane 1,2-dicarboxylic acid
cyclohex-4-ene 1,2-dicarboxylic acid
norbornane dicarboxylic acid
norbornene dicarboxylic acid
phthalic acid A preferred group of such compounds is the 1,1'-alkanoyl bis(2,2,4,4,6-pentamethyl hexahydropyrimidines).

EXAMPLE 10

Acylation of Cyclohexyl Analog of a HHP with Octanoyl Chloride

To a stirred solution of 8.29 g. (0.030 mole) of 2,4-dipentamethylene-5,6-tetramethylene hexahydropyrimidine (see Example 7) in 150 ml. dry toluene, a solution of 4.88 g. (0.0303 mole) n-octanoyl chloride in 50 ml. dry toluene was added and stirred overnight, followed by refluxing for 7 hours. The solvent was removed, and the resulting brown oil taken up in heptane, washed with saturated aqueous sodium bicarbonate solution, and the heptane removed. The resulting oil was digested with 5% aqueous sodium hydroxide, and extracted with methylene chloride. The methylene chloride extracts were washed with water, dried, and the solvent removed to give 7.46 g. (61.8% yield) of a viscous brown oil, partly solidifying on standing.

The product can be represented by the following formula and name:

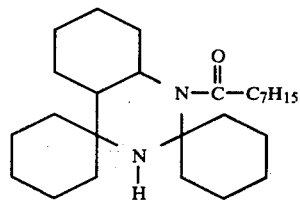

14-n-octanoyl-15,16-tetramethylene-7,14-diazadispiro[5.1.5.3]hexadecane, hereafter referred to as Compound 10.

By substituting an equivalent amount of propionyl chloride for the octanoyl chloride used in the above example, there is produced: 14-n-propionyl-15,16-tetramethylene-7,14-diazaspiro[5.1.5.3]hexadecane. Similarly, other members of the group can be produced, identified as 14-n-alkanoyl-15,16-tetramethylene-7,14-diazaspiro[5.1.5.3] hexadecane.

EXAMPLE 11

Reaction of a HHP with Isophorone Diisocyanate to form a Bis-Urea

A solution of 10.4 gm. (0.0667 mole) of 2,2,4,4,6-pentamethylhexahydropyrimidine, in 10 ml. of tetrahydrofuran, was added dropwise to a solution of 7.41 gm. (0.0333 mole) of isophorone diisocyanate in 40 ml. tetrahydrofuran resulting in an exothermic reaction. The resulting mixture was refluxed an additional 5 hours after which the tetrahydrofuran was removed and the residue triturated with heptane. The resulting product was a fluffy white solid (13.46 g., 75.5%), with a m.p. of 221°–4°. It can be depicted by the formula:

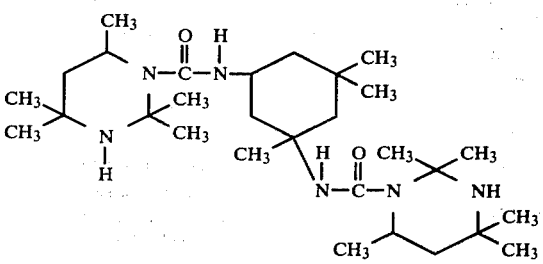

and described by the name:

3-carboxy[2,2,4,4,6-pentamethylhexahydropyrimidin-1-yl]-aminomethyl-1-carboxy[2,2,4,4,6-pentamethylhexahydropyrimidin-1-yl]amino-3,3,5-trimethyl cyclohexane, hereafter, Compound 11.

By substituting an equivalent amount of hexamethylene diisocyanate for the isophorone diisocyanate used above, there is obtained N,N'-hexamethylene bis(3-carboxy(2,2,4,4,6-pentamethylhexahydropyrimidin-1-yl)diamine.

EXAMPLE 12

Reaction of a HHP with a Benzoyl Chloride Derivative

To a solution of 3,5-di-t-butyl-4-hydroxy-benzoyl chloride, in 150 ml. toluene—prepared from 10 gm. (0.0442 mole) of 3,5-di-t-butyl-4-hydroxybenzoic acid and thionyl chloride—was added dropwise 6.9 gms. (0.0442 mole) of 2,2,4,4,6-pentamethylhexahydropyrimidine in 100 ml. toluene. A precipitate resulted. The mixture was refluxed for 2 hours and filtered. The precipitate was triturated with saturated aqueous sodium bicarbonate, filtered, washed with water and dried, yielding 14.0 g. (87%) of a product having a m.p. of 255°–257° C. The product and be repesented by the formula:

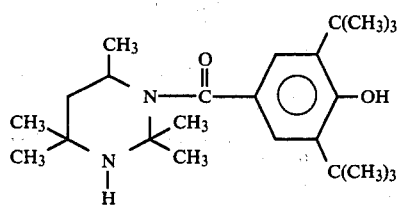

and can be described by the name:

1-(3,5-di-tert-butyl-4-hydroxy benzoyl)-2,2,4,4,6-pentamethyl hexahydropyrimidine, hereafter, Compound 12.

By subsituting an appropriate amount of benzoyl chloride for the 3,5-di-t-butyl-4-hydroxybenzoyl chloride, there is produced: 1-(benzoyl)-2,2,4,4,6-pentamethyl HHP.

EXAMPLE 13

Reaction of a HHP with Succinic Anhydride 1.95 g. (0.0195 mole) of succinic anhydride was dissolved in hot xylene. To the hot xylene solution, 3 g. (0.0195 mole) of 2,2,4,4,6-pentamethyl hexahydropyrimidine was added dropwise, resulting in an exothermic reaction and the formation of a precipitate. The mixture was then refluxed for 2 hours, cooled, and the precipitate collected, washed and dried, yielding 4.01 g. (80% yield) of an off-white amorphous solid, m.p. 310° C. (dec.), with the formula:

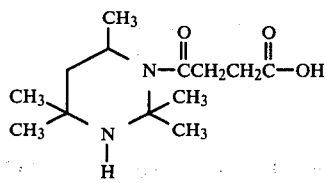

The salts of Ni, Ba, and Co of this acid are also useful as light stabilizing additives.

EXAMPLE 14

Reaction of a HHP with Octadecylisocyanate to Form a Urea

A solution of 4.72 g (0.0303 mole) of 2,2,4,4,6-pentamethylhexahydropyrimidine in 15 ml dry tetrahydrofuran was added dropwise to a solution of 8.91 g (0.0303 mole) n-octadecylisocyanate, resulting in an exothermic reaction. This mixture was refluxed for two hours, cooled, the solvent removed, and the resulting solid crystallized from heptane to give a fluffy white solid, 1-(octadecylamino carbonyl) 2,2,4,4,6-pentamethyl HHP, hereafter Compound 14, (10.9 g, 90.1% yield), with a m.p. 70°–72° C., which can be depicted by the formula:

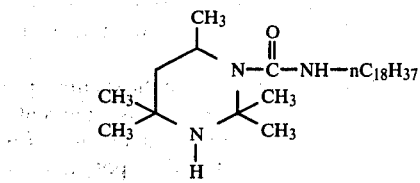

By substituting other alkylisocyanates for the octadecylisocyanate used in this example, other alkylamino compounds may be prepared in similar fashion.

GENERAL

Other compounds that are representative of the light stabilizers of the invention are identified as follows:

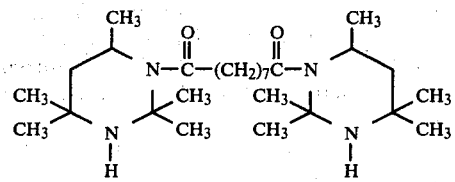

1,1'-azelaoyl bis(2,2,4,4,6-pentamethyl hexhydropyrimidine), hereafter referred to as Compound 21-1, and:
2,2,4,6-tetramethyl 6-ethyl-5-lauroyl HHP
2,2,4,6-tetramethyl 6-n-butyl-5-benzoyl HHP
5-octadecanoyl-2,2,4-trimethyl-1,5-diaza spiro [5.5] undecane
2,2,4,6-tetramethyl 6-phenyl 5-lauroyl HHP
2,2,4-trimethyl 6,6-phenyl-5-lauroyl HHP
2,2,4,6-tetramethyl 6(1-naphthyl)-5-octanoyl HHP
2,2,4,6-tetramethyl 6(4-methyl phenyl) 5-octanoyl HHP
2,2,4,6-tetramethyl 6(4-methoxy phenyl) 5-octanoyl HHP
2,2,4,6-tetramethyl 6-benzyl 5-octanoyl HHP
2,2,3,6,6-pentamethyl-4-ethyl-5-decanoyl HHP
2,2,4,6,6-pentamethyl-3-propionyl HHP
1-(ethoxycarbonyl)-2,2,4,4,6-pentamethyl HHP
1-(phenoxy)-2,2,4,4,6-pentamethyl HHP
3-hydroxy-1-stearoyl-2,2,4,4,6-pentamethyl HHP
3-benzyl-1-stearoyl-2,2,4,4,6-pentamethyl HHP
3-ethyl-1-stearoyl-2,2,4,4,6-pentamethyl HHP
1,3-di-octanoyl-2,2,4,4,6-pentamethyl HHP
3-oxyl-1-stearoyl-2,2,4,4,6-pentamethyl HHP
1,3-di-benzoyl-2,2,4,4,6-pentamethyl HHP These can be prepared by following the techniques in the examples above.

The acylated hexahydropyrimidines of this invention are resistant to hydrolysis and are very stable during storage and processing, as compared to the hexahydropyrimidines. In addition, the compounds of the invention can be prepared to have relatively high molecular weights and desirably low volatility.

The compounds of this invention are utilized as ultraviolet (uv) stabilizers for synthetic polymers. They are used by themselves or in conjunction with other ultraviolet stabilizers and/or antioxidants.

A compound of this invention, when used as the only ultra-violet stabilizer, may be present in the polymer in a very small but effective amount, in the range from about 0.05 wt. percent to about 1.0 wt. percent, based on the polymer. When utilized in conjunction with other uv stabilizers, the total amount of uv stabilizer present is in the range of about 0.1 wt. percent to about 3.0 wt. percent, of which a compound or compounds of this invention preferably amounts to from about 10 percent to about 90 percent of the total amount of uv stabilizers.

When antioxidants are utilized the antioxidant is present in an amount of from about 0.025 wt. percent to about 5 wt. percent, and preferably from about 0.01 wt. percent to about 2 wt. percent, based on polymer. Preferred antioxidants are the hindered phenolic antioxidants already mentioned.

To illustrate the effectiveness of the compounds of this invention, the following polymer composition was prepared:

One thousand (1000) parts of polypropylene (Profax 6501, Hercules) was mixed with one part of tris-(3,5-di-tertiarybutyl-4-hydroxybenzyl)isocyanurate (Goodrite 3114, Goodrich) and 0.5 parts of calcium stearate. To this mixture was added 2.5 parts or 5 parts (as shown in Table 1 below) of the light stabilizer, dissolved in 100 ml. of methylene chloride. The mixture was stirred for 15 to 20 minutes and the methylene chloride allowed to evaporate.

The resultant powder was dried, and then extruded into a 3/32 inch strand. The strand was then cut into pellets. The pellets were dried and then extruded into a broad (8″) band through an extruder. The extruded band (film) was slit and a ¼″ section of the film was oriented by drawing it at 175° F. at a 7:1 draw ratio. The dimensions of the oriented film were about 1×80 mils.

The several oriented film specimens thus prepared were mounted on aluminum frames and exposed in an Atlas Weather-Ometer, Model 65 WR. At regular intervals, the test specimens were removed from exposure and their tensile strength measured on an Instron tensile tester. The results are recorded in Table 1.

A decrease in tensile strength, expressed as tenacity, over the tensile strength of the same formulation before exposure, is a measure of the deterioration of the physical properties of the polymer. "Failure" in this test is defined as a loss of 50% or more of the sample's tenacity, after exposure.

TABLE 1

| | Stabilization Effectiveness | |
|---|---|---|
| Compound | % of Light Stabilizer Added, Based on Polymer | Time to Failure (hrs.) |
| 8 | 0.25% | 1765 |
| | 0.50% | 2095 |
| 11 | 0.25% | 1750 |
| | 0.50% | 1935 |
| 12 | 0.25% | 850 |
| Blank (anti- | | |

TABLE 1-continued

| | Stabilization Effectiveness | |
|---|---|---|
| Compound | % of Light Stabilizer Added, Based on Polymer | Time to Failure (hrs.) |
| oxidant only) | — | 450 |

A review of Table 1 shows that film stabilized with an antioxidant only, without any addition of the light stabilizers of this invention, "failed" in 450 hours, about one-half to one-fourth the time for the samples with light stabilizer to fail.

A second series of tests was conducted in the same way. The results are summarized in Table 2 below.

TABLE 2

| Additional Demonstrations of Stabilization Effectiveness | | |
|---|---|---|
| Compound | % of Light Stabilizer Added Based on Polymer | Time to Failure (hrs.) |
| 9 | 0.25% | 2920 |
| | 0.5% | 4300 |
| | 0.25 + 0.25 AM340* | 3420 |
| 14 | 0.25% | 2210 |
| | 0.5% | 3520 |
| | 0.25 + 0.25 AM340 | 2440 |
| 12 | 0.25% | 2440 |
| | 0.5% | 2210 |
| | 0.25 + 0.25 AM340 | 2480 |
| 10 | 0.25% | 540 |
| | 0.5% | 320 |
| | 0.25 + 0.25 AM340 | 890 |
| 21-1 | 0.25% | 2310 |
| | 0.5% | 4400+ |
| | 0.25 + 0.25 AM340 | 2930 |
| 11 | 0.25% | 1790 |
| | 0.5% | 2430 |
| | 0.25 + 0.25 AM340 | |
| Blank | — | 640 |

*AM340 is a commercially available stabilizer, having the formula 2,4-di-t-butyl-phenyl-3,4-di-t-butyl-4-hydroxy benzoate.

The results obtained with Compound 10 appear to be anomolous.

A pronounced mutual enhancement (synergism) between the compounds of the invention and the AM340 commercial stabilizer is shown by these tests. This behavior is typical of the acylated hexahydropyrimidines of this invention.

The foregoing examples are exemplary rather than limiting. The appended claims are intended to encompass all modifications that would readily occur to those of ordinary skill in the art and are not to be limited except as expressly stated therein.

What is claimed is:

1. An acylated, hindered hexahydropyrimidine of the formula

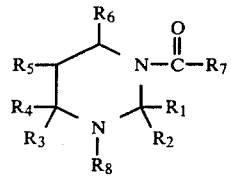

wherein
$R_1$, $R_2$, $R_3$ and $R_4$ may be the same or different independently of each other and are selected from the group consisting of: alkyl having 1 to 6 carbon atoms, when unsubstituted, or substituted with one methyl, ethyl, or phenyl group, aryl, and aryl substituted with 1 to 3 substituents selected from the group consisting of lower alkyl, lower alkoxy, and hydroxyl, and wherein $R_1$ together with $R_2$, and $R_3$ together with $R_4$, each taken together with the respective ring carbon to which they are attached, may form respectively a cycloalkyl of ring size from 4 to 7 carbons;

$R_5$ and $R_6$ may be the same or different and are selected from the group consisting of hydrogen, and alkyl having 1 to 6 carbon atoms, and arylalkyl, and $R_5$ together with $R_6$ and the two ring carbons to which they are attached respectively may form a cycloalkyl group of ring size from 5 to 7 carbon atoms;

$R_7$ is selected from the group consisting of: alkyl having 1 to 20 carbon atoms, substituted alkyl where the alkyl without substitution has 1 to 20 carbon atoms and where substituents may be up to five lower alkyl groups, arylalkyl, cycloalkyl having 3 to 12 carbon atoms, aryl, aryl substituted with 1 to 3 substituents selected from the group consisting of: lower alkyl, lower alkoxy, and hydroxyl;

$$-OR_9, -NHR_9, -ACOR_{10}, \text{ and } -\underset{H}{N}ANHCOR_{10},$$

wherein $R_9$ is selected from the group consisting of alkyl having 1 to 20 carbon atoms unsubstituted, or substituted with up to 5 lower alkyl groups, and cycloalkyl having 5 to 11 carbons and phenyl; wherein A is: alkylene of 1 to 12 carbons; alkylene substituted with alkyl or alkenyl to have a total of up to 18 carbons; alkenylene of 2 to 4 carbons; cycloalkylene of up to 12 carbon atoms; cycloalkenylene of up to 12 carbon atoms; bicycloalkylene up to 8 carbon atoms; bicycloalkenylene up to 8 carbon atoms; or phenylene, and wherein $R_{10}$ is selected from the group consisting of hydroxyl, lower alkoxy, phenoxy and the group

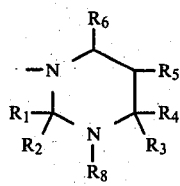

wherein $R_1, R_2, R_3, R_4, R_5$ and $R_6$ are as defined above, and $R_8$ is selected from the group consisting of hydrogen, alkyl having 1 to 10 carbon atoms, substituted alkyl having 1 to 10 carbon atoms, arylalkyl, hydroxyl, oxyl and

wherein $R_{11}$ is selected from the group consisting of alkyl having 1 to 20 carbon atoms unsubstituted, or substituted with up to five alkyl groups wherein the substitution in substituted alkyl consists of from 1 to 3 substituent alkyl groups of up to 18 carbons each, which substituent groups may be the same or different, and wherein the substitution in substituted aryl consists of from 1 to 3 substituent groups that may be the same or different and that are selected from the group consisting of hydroxyl and lower alkyl.

2. An acylated, hindered hexahydropyrimidine salt according to claim 1 comprising a nickel, cobalt, or barium salt of the acylated hexahydropyrimidine where $R_{10}$ is hydroxyl before formation of the salt.

3. An acylated, hindered hexahydropyrimidine according to claim 1 wherein $R_1, R_2, R_3$, and $R_4$ may be the same or different and are selected from the group consisting of alkyl having 1 to 6 carbon atoms, and $R_1$ together with $R_2$, and $R_3$ together with $R_4$, each taken together with the respective ring carbon to which they are attached, may form respectively a cycloalkyl group of 5 to 6 carbons;

$R_5$ and $R_6$ may be the same or different and are selected from the group consisting of hydrogen and alkyl having 1 to 6 carbon atoms, and $R_5$ together with $R_6$ and the two ring carbons to which they are attached respectively may form a cycloalkyl group having 5 to 6 carbons;

$R_7$ is selected from the group consisting of alkyl having 1 to 20 carbon atoms, substituted alkyl where the alkyl without substitution has 1 to 20 carbon atoms and where the substituents may be up to five lower alkyl groups, arylalkyl, aryl, aryl substituted with 1 to 3 substituents selected from the group consisting of lower alkyl, lower alkoxy, and hydroxyl; $-OR_9$, $-NHR_9$, the group $-(CH_2)_nCOR_{10}$ where n is 1 to 20, and

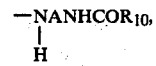

wherein $R_9$ is selected from the group consisting of alkyl having 1 to 20 carbon atoms and phenyl, and $R_8$ is selected from the group consisting of hydrogen, lower alkyl, hydroxyl, oxyl and

wherein $R_{11}$ is selected from the group consisting of alkyl having 1 to 20 carbon atoms unsubstituted, or substituted with up to five lower alkyl groups.

4. An acylated hindered hexahydropyrimidine according to claim 1 wherein each of $R_1, R_2, R_3, R_4$ and $R_6$ is methyl, $R_5$ is hydrogen, $R_7$ is selected from the group consisting of: alkyl having 1 to 20 carbon atoms unsubstituted, or substituted with up to five lower alkyl groups, aryl, aryl substituted with 1 to 3 substituents selected from the group consisting of lower alkyl, lower alkoxy, and hydroxyl, $-OR_9$, $-NHR_9$ and the group $-CH_2COR_{10}$, wherein $R_9$ is selected from the group consisting of alkyl having 1 to 20 carbon atoms and phenyl, and $R_{10}$ is the group

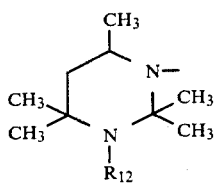

wherein $R_{12}$ is selected from the group consisting of hydrogen, lower alkyl, hydroxyl and oxyl.

5. An acylated hindered hexahydropyrimidine according to claim 1 wherein the compound has the formula

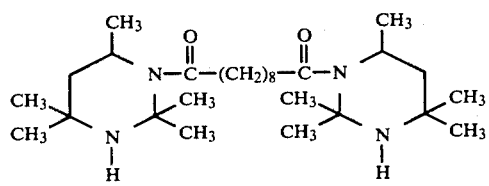

6. An acylated hindered hexahydropyrimidine according to claim 1 wherein the compound has the formula

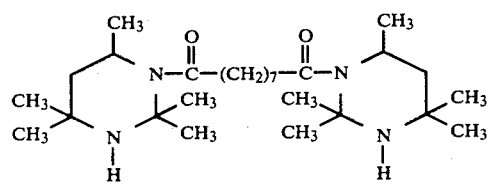

7. An acylated hindered hexahydropyrimidine according to claim 1 wherein the compound has the formula

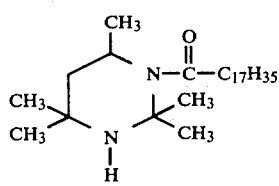

8. An acylated hindered hexahydropyrimidine according to claim 1 wherein the compound has the formula

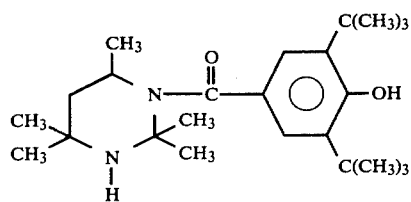

9. An acylated hindered hexahydropyrimidine according to claim 1 wherein the compound has the formula

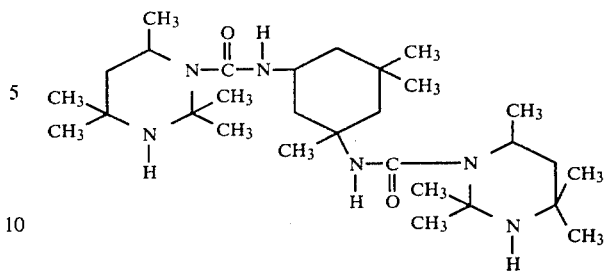

10. A synthetic polymeric composition comprising an amount effective as a light stabilizer of an acylated, hindered hexahydropyrimidine according to claim 1, 2, 3, 4, 5, 6, 7, or 8.

11. A polymeric composition containing a light stabilizing amount of an acylated hindered hexahydropyrimidine according to claim 9 wherein the polymer comprises a homopolymer of a vinyl halide, a copolymer of a vinyl halide with at least one other polymerizable unsaturated compound, a homopolymer of an alpha olefin, a copolymer of alpha olefins, a polydiene, a polyurethane, a polyamide, a polycarbonate, a polyacetal, polystyrene, acrylonitrile-butadiene-styrene, a copolymer of a vinyl halide with an olefin, or copolymers or mixtures thereof.

12. A polymeric composition containing a light stabilizing amount of an acylated hindered hexahydropyrimidine according to claim 11 wherein the polymer is a poly$\alpha$-olefin.

13. A polymeric composition containing a light stabilizing amount of an acylated hindered hexahydropyrimidine according to claim 3 wherein the polymer is selected from the group consisting of polymers and copolymers of ethylene, propylene, butene, and mixtures thereof.

14. A polymeric composition containing a light stabilizing effective amount of an acylated hindered hexahydropyrimidine according to claim 13 wherein the polymer is polypropylene.

15. A method of light stabilizing polymeric compositions by incorporating therein an effective amount of an acylated hindered hexahydropyrimidine according to claim 1, 2, 3, 4, 5, 6, 7, or 8.

16. A method of light stabilizing a polymeric composition selected from the group consisting of polyvinyl chloride, poly$\alpha$-olefins, polydienes, polyurethanes, polyamides, polycarbonates, polyacetals, polystyrene, acrylonitrile-butadiene-styrene and copolymers of vinyl halides with olefins, by incorporating therein an effective amount of an acylated hindered hexahydropyrimidine according to claim 1, 2, 3, 4, 5, 6, 7, or 8.

17. A method of light stabilizing a polymeric composition in accordance with claim 15 wherein the polymer is a poly$\alpha$-olefin.

18. A method of light stabilizing a polymeric composition in accordance with claim 17 wherein the polymer is selected from the group consisting of polymers and copolymers of propylene and butene.

19. A method of light stabilizing a polymeric composition in accordance with claim 17 wherein the polymer is a polymer of propylene.

20. 1-(alkanoyl)2,2,4,4,6-pentamethyl hyexahydropyrimidine.

21. 1-(stearoyl)2,2,4,4,6-pentamethyl hexahydropyrimidine.

22. 1-(propionyl)2,2,4,4,6-pentamethyl hexahydropyrimidine.

23. 1-(cyclohexane carbonyl)2,2,4,4,6-pentamethyl hexahydropyrimidine.

24. 1,1'-alkanoyl bis(2,2,4,4,6-pentamethyl hexahydropyrimidine).

25. 1,1'-sebacoyl bis(2,2,4,4,6-pentamethyl hexahydropyrimidine).

26. 14-n-alkanoyl-15,16-tetramethylene-7,14-diazaspiro[5.1.5.3]hexadecane.

27. 3-carboxy[2,2,4,4,6-pentamethylhexahydropyrimidin-1-yl]amino methyl-1-carboxy[2,2,4,4,6-pentamethylhexahydropyrimidin-1-yl]amino-3,3,5-trimethyl cyclohexane.

28. A 1-(3,5-benzyl)-2,2,4,4,6-pentamethyl hexahydropyrimidine.

29. A compound of claim 28 wherein the benzoyl is a di-t-butyl-4-hydroxy benzoyl.

30. The reaction product of a dibasic carboxylic acid or dibasic carboxylic acid anhydride with a hindered hexahydropyrimidine.

31. A product of claim 30 wherein the acid anhydride is succinic anhydride.

32. A product of claim 31 wherein the hindered hexahydropyrimidine is 2,2,4,4,6-pentamethyl hexahydropyrimidine.

33. The nickel, cobalt or barium salt of the product of claim 30, 31 or 32.

34. 1-(alkylamino carbonyl)2,2,4,4,6-pentamethyl hexahydropyrimidine.

35. 1-(octadecylamino carbonyl)2,2,4,4,6-pentamethyl hexahydropyrimidine.

* * * * *